(12) United States Patent
Shibuya

(10) Patent No.: US 11,409,192 B2
(45) Date of Patent: Aug. 9, 2022

(54) MAGNETICALLY SHIELDED ROOM

(71) Applicant: TDK Corporation, Tokyo (JP)

(72) Inventor: Tomohiko Shibuya, Tokyo (JP)

(73) Assignee: TDK Corporation, Tokyo (JP)

( * ) Notice: Subject to any disclaimer, the term of this patent is extended or adjusted under 35 U.S.C. 154(b) by 355 days.

(21) Appl. No.: 16/618,884

(22) PCT Filed: May 31, 2018

(86) PCT No.: PCT/JP2018/020878
§ 371 (c)(1),
(2) Date: Dec. 3, 2019

(87) PCT Pub. No.: WO2018/225608
PCT Pub. Date: Dec. 13, 2018

(65) Prior Publication Data
US 2020/0096855 A1    Mar. 26, 2020

(30) Foreign Application Priority Data

Jun. 7, 2017  (JP) .............................. JP2017-112732
Jan. 15, 2018 (JP) ................................. 2018-004571

(51) Int. Cl.
*G03B 29/00* (2021.01)
*E04B 1/343* (2006.01)
(Continued)

(52) U.S. Cl.
CPC .............. *G03B 29/00* (2013.01); *A61B 5/055* (2013.01); *E04B 1/34336* (2013.01); *E04B 1/92* (2013.01);
(Continued)

(58) Field of Classification Search
USPC ........................................................ 600/411
See application file for complete search history.

(56) References Cited

U.S. PATENT DOCUMENTS 5,134,373 A * 7/1992 Tsuruno ............... G01R 33/283
324/309
7,823,306 B1 * 11/2010 Kersten ............. A61M 21/0094
40/436
(Continued)

FOREIGN PATENT DOCUMENTS

JP   2002-34945 A   2/2002
JP   2003180646 A   7/2003
(Continued)

OTHER PUBLICATIONS

International Search Report in International Application No. PCT/JP2018/020878, dated Aug. 14, 2018.

*Primary Examiner* — Rodney E Fuller
(74) *Attorney, Agent, or Firm* — Leydig, Voit & Mayer, Ltd.; John Augustyn

(57) ABSTRACT

A magnetically shielded room reducing pressure felt by a person inside includes an upper shielding body, a side periphery shielding body, and a lower shielding body, all of which define a magnetically shielded inner space. A magnifying lens is located in the upper shielding body. The magnifying lens can magnify and project an incident image from outside to a range of one inner side surface of the magnetically shielded room. so that the range should be 50% or more of the area of the one inner side surface. The range includes most of the area above a line of sight of a person in the magnetically shielded room. The magnifying lens is provided at a position closer to the one inner side surface as a projection target of the lens than the other inner side surface as a non-projection target facing the one inner side surface as the projection target.

12 Claims, 5 Drawing Sheets

(51) Int. Cl.
  *E04B 1/92*   (2006.01)
  *G01R 33/00*  (2006.01)
  *G03B 21/62*  (2014.01)
  *G02B 25/00*  (2006.01)
  *G03B 35/24*  (2021.01)
  *E04H 3/08*   (2006.01)
  *G21F 7/02*   (2006.01)
  *A61B 5/055*  (2006.01)

(52) U.S. Cl.
  CPC ........... *E04H 3/08* (2013.01); *G01R 33/0076* (2013.01); *G02B 25/002* (2013.01); *G03B 21/62* (2013.01); *G03B 35/24* (2013.01); *G21F 7/02* (2013.01)

(56) References Cited

U.S. PATENT DOCUMENTS

| | | | |
|---|---|---|---|
| 9,140,965 B2 * | 9/2015 | Dennis | G03B 21/62 |
| 2003/0114745 A1 | 6/2003 | Amano et al. | |
| 2006/0178597 A1 * | 8/2006 | Fujimaki | A61B 5/378 |
| | | | 600/558 |
| 2017/0123020 A1 * | 5/2017 | Ohmure | G01R 33/283 |

FOREIGN PATENT DOCUMENTS

| | | |
|---|---|---|
| JP | 2004-160086 A | 6/2004 |
| JP | 2005-131122 A | 5/2005 |
| JP | 2015114579 A | 6/2015 |
| JP | 2015142157 A | 8/2015 |
| JP | 2015-198724 A | 11/2015 |

\* cited by examiner

1 Magnetically Shielded Room

1 Magnetically Shielded Room

MAGNETICALLY SHIELDED ROOM

TECHNICAL FIELD

The present invention relates to a magnetically shielded room used for various magnetic measurements.

BACKGROUND ART

Patent Document 1 below discloses that a projector arranged outside of a shielded room for biomagnetic measurement projects an image required by an examiner and an image for a tester to view into the shielded room. According to this, it is said that the examiner can use the image projected for positioning of the tester, and it is not necessary to perform a wasteful operation such as going back and forth inside and outside the shielded room. Also, an image that distracts the tester can be shown to the tester, and the tester's fear and tension of the measurement can be reduced.

Patent Document 2 below relates to an optical device for a magnetically shielded room in a visual magnetoencephalograph which presents an image to a tester in the magnetically shielded room and measures magnetoencephalograms induced by applying visual stimuli to the tester. Patent Document 2 discloses that the image from a projector outside of the magnetically shielded room is projected from the outside of the magnetically shielded room onto a screen inside the magnetically shielded room by using the lens system.

PRIOR ART DOCUMENT

Patent Document

Patent Document 1 Japanese Laid-Open Patent Publication No. 2003-180646.
Patent Document 2 Japanese Laid-Open Patent Publication No. 2002-34945

SUMMARY OF THE INVENTION

Problem to be Solved by the Invention

In the conventional magnetically shielded room, the image is only projected to a local range compared to a size of an inner wall surface, so there is a possibility that a person inside the magnetically shielded room may feel a sense of pressure in a closed space. In a small magnetically shielded room, this feeling of pressure may be felt even stronger.

The present invention was made in view of this situation and it is an object of the present invention to provide a magnetically shielded room that can reduce the feeling of pressure felt by a person inside.

Means for Solving Problem

An aspect of the present invention is a magnetically shielded room. The magnetically shielded room comprises:
an upper shielding body, a side periphery shielding body and a lower shielding body, all of which define a magnetically shielded inner space; and
a magnifying lens provided in at least one of the upper shielding body and the lower shielding body; wherein
the magnifying lens can magnify and project an image projected from outside on at least one inner side surface of the magnetically shielded room, or a transparent or translucent film or sheet which extends in vertical direction or obliquely up and down in the magnetically shielded room.

Another aspect of the present invention is a magnetically shielded room. The magnetically shielded room comprises:
an upper shielding body, a side periphery shielding body, and a lower shielding body, all of which define a magnetically shielded inner space;
a partition member, wherein the inner space is divided into first and second inner spaces by the partition member which is magnetically shielding body;
a projection device provided in the second inner space; and
a magnifying lens provided in the partition member; wherein
the magnifying lens can magnify and project an image projected from the projection device on at least one inner side surface of the magnetically shielded room facing the first inner space, or a transparent or translucent film or sheet which extends in vertical direction or obliquely up and down in the first inner space.

The magnifying lens may be provided at a position closer to the one inner side surface as a projection target of the lens than the other inner side surface as a non-projection target facing the one inner side surface as the projection target.

The magnifying lens may be provided corresponding to each of a plurality of the inner side surfaces of the magnetically shielded room.

The other aspect of the present invention is a magnetically shielded room. The magnetically shielded room comprises:
an upper shielding body, a side periphery shielding body, and a lower shielding body, wherein
a magnifying lens is provided in the upper shielding body, and
the magnifying lens can magnify and project an image projected from outside over the entire circumference of all inner side surfaces of the magnetically shielded room.

An image of outside of the magnetically shielded room may be projected by the magnifying lens.

The magnifying lens may include a right-eye magnifying lens that projects a right-eye image and a left-eye magnifying lens that projects a left-eye image.

At least a projection range of the inner side surface that is a projection target of the magnifying lens may be covered with wallpaper or material suitable for projecting the image.

The magnetically shielded room may be movable.

It is to be noted that any arbitrary combination of the above-described structural components as well as the expressions according to the present invention changed among a system and so forth are all effective as and encompassed by the present aspects.

Effect of the Invention

According to the present invention, there is provided a magnetically shielded room that can reduce the feeling of pressure felt by a person inside.

EMBODIMENTS FOR CARRYING OUT THE INVENTION

Figure 1:
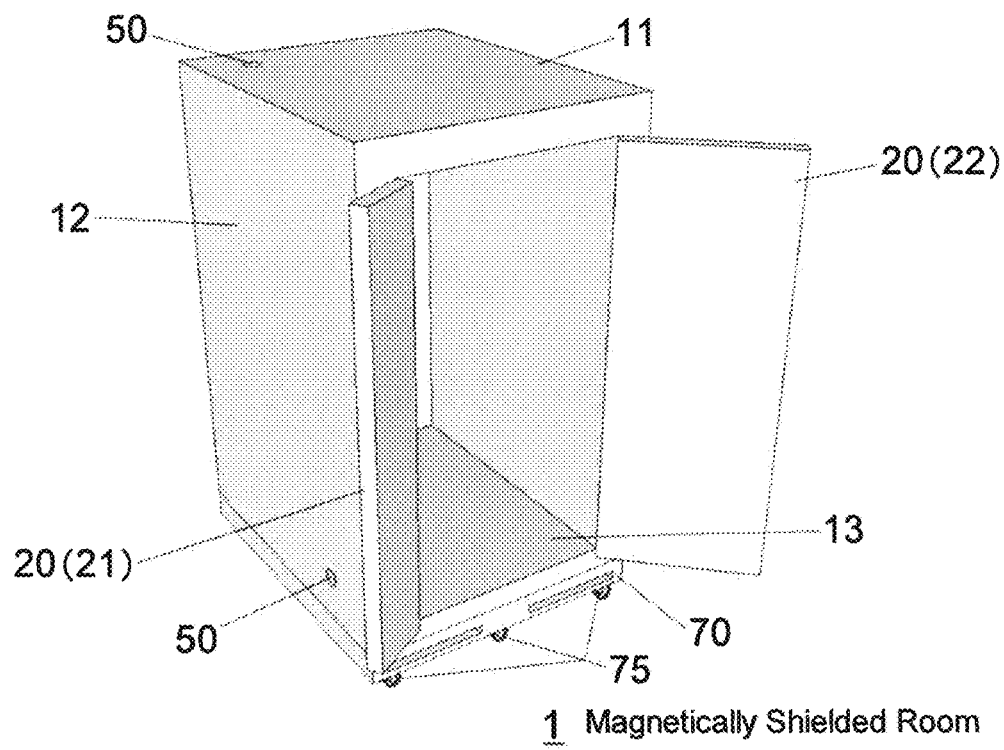
FIG. 1 is a perspective view seen from the front upper left direction of a first embodiment of a magnetically shielded room 1 according to the present invention.
Figure 2:
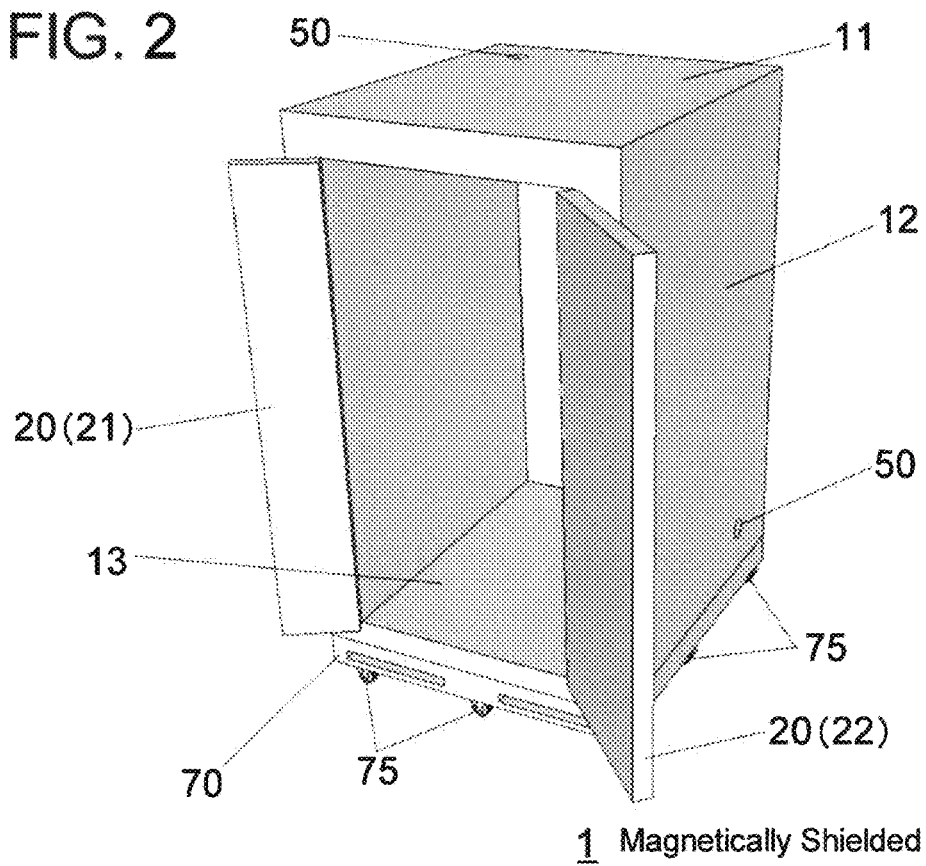
FIG. 2 is a perspective view seen from the front upper right direction of the first embodiment.
Figure 3:
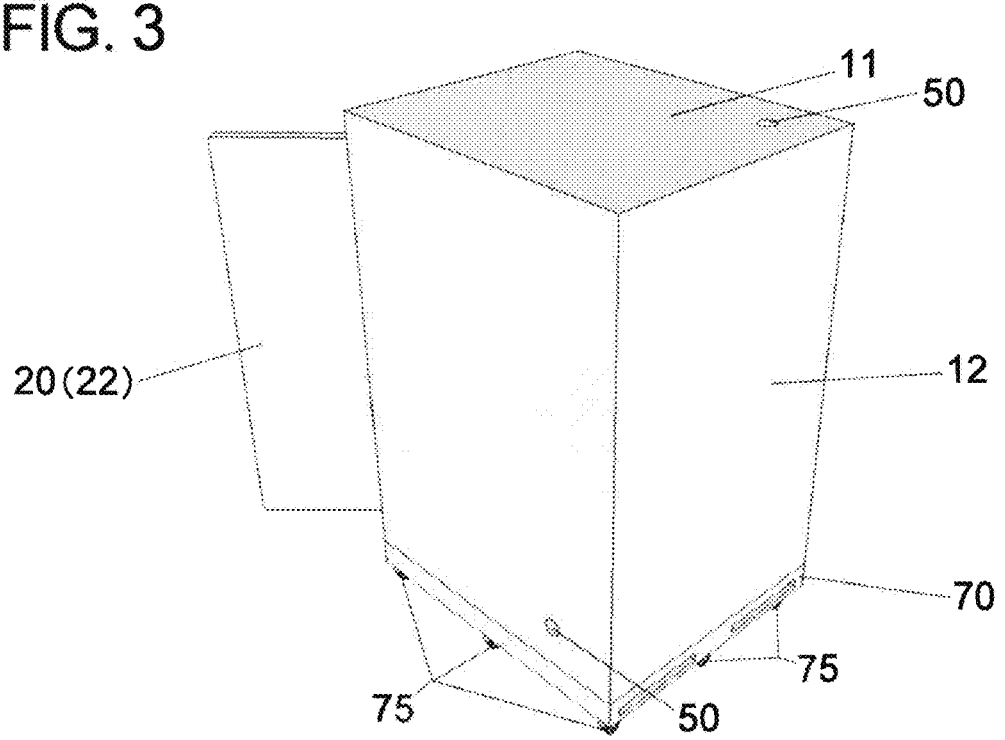
FIG. 3 is a perspective view seen from the rear upper left direction of the first embodiment.
Figure 4:
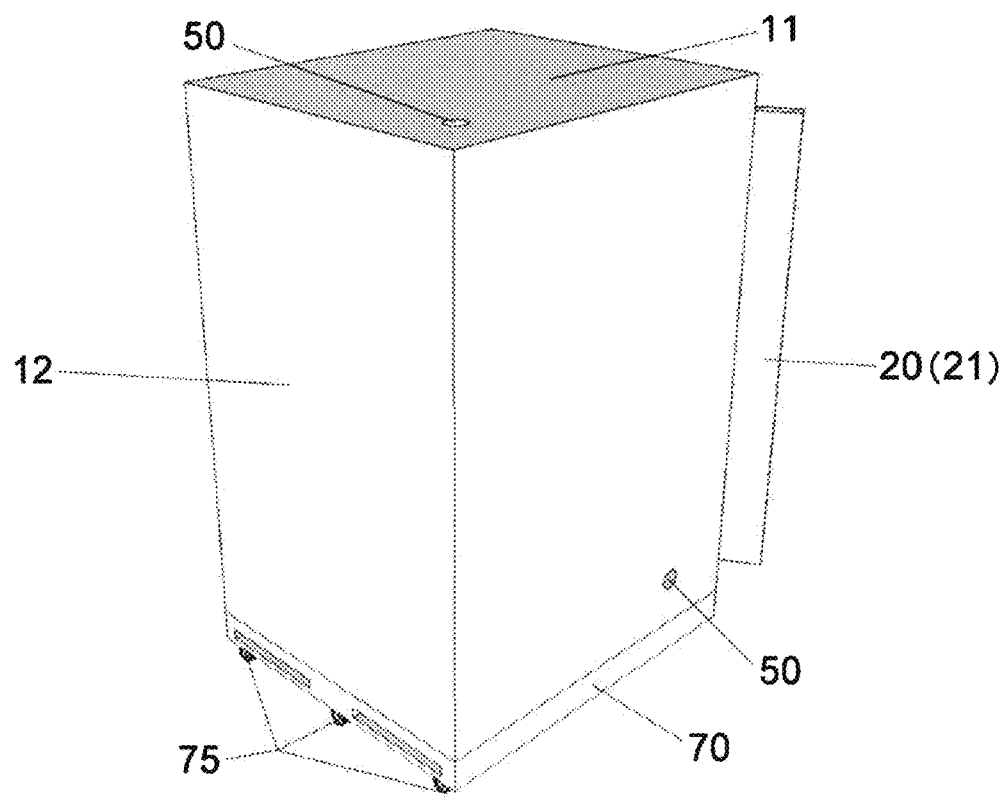
FIG. 4 is a perspective view seen from the rear upper right direction of the first embodiment.

Preferred embodiments of the present invention will now be described in detail with reference to the drawings. The same or equivalent constituent parts, members, etc., shown in the drawings are designated by the same reference numerals and will not be repeatedly described as appropriate. The embodiments are not intended to limit the invention but are mere exemplifications, and all features or combinations thereof described in the embodiments do not necessarily represent the intrinsic natures of the invention.

First Embodiment

A first embodiment of the magnetically shielded room 1 according to the present invention will be described with reference to FIGS. 1 to 5. The magnetically shielded room 1 has an upper shielding body 11, a side periphery shielding body 12, a lower shielding body 13, and a door 20 for opening and closing an opening in the side wall. The door 20 may be a single door but consists a double door of a left door 21 and a right door 22 in this embodiment.

They are connected to the left and right edge parts of the opening in the side periphery shielding body 12 by unshown hinges, respectively, in such a manner that they can open and close. The upper shielding body 11 is provided with a through hole 50 to pass through a projection light of an image from a projection device (projector) 51 installed outside the magnetically shielded room 1. Through hole 50 may be also formed in the side periphery shielding body 12 and the lower shielding body 13 as necessary, for letting wirings connected to the unshown measurement equipment and the power cords and cables of the unshown supplementary equipment pass therethrough. A pipe-like through conductor unshown may be provided on at least part of the through hole 50, so that it conducts with a conductor plate (for example, a magnetic material layer or a high conductivity material layer described later) of the upper shielding body 11, the side periphery shielding body 12 or the lower shielding body 13. Thereby, leakage of electromagnetic wave noise from the through hole 50 can be reduced.

A pedestal 70 having the same size as the bottom surface of the lower shield body 13 and higher rigidity than the lower shield body 13 is provided on the bottom side (under surface) of the lower shield body 13 to mount and fix the lower shield body 13 thereon. The pedestal 70 is made of, for example, stainless steel. At least three casters 75 are attached to the bottom surface of the pedestal 70 as moving means for moving over the floor. In the embodiment, the magnetically shielded room 1 is movable and provided with the castors 75, which is convenient at the time of moving. At least one, preferably two or more of the casters 75 may be provided with a stopper. Preferably, the upper shield body 11, the side periphery shield body 12, and the lower shield body 13 are conductively connected to the pedestal 70 (electrically connected to have the same potential). The pedestal 70 may be made of a non-magnetic material having high rigidity and non-conductivity.

The upper shielding body 11, the side periphery shielding body 12, the lower shielding body 13 and the door 20 are a magnetically shielding body which can shield a magnetic field noise and an electromagnetic noise. Hereinafter, each of the upper shielding body 11, the side periphery shielding body 12, the lower shielding body 13 and the door 20 is also simply written as "shielding body". Each shielding body includes at least one magnetic material layer and, as necessary, a high conductivity material layer. Preferably, each shielding body has two magnetically shielding layers which consist of a magnetic material layer and a high conductivity material layer, and also has a layer of non-high conductivity and non-magnetic, such as a wood layer or air layer between said two magnetically shielding layers. The magnetic material layer is, for example, a permalloy plate as a conductor of high permeability. The high conductivity material layer is, for example, an aluminum plate as a conductor. The permalloy plate is effective to shield magnetic field noise. The aluminum plate is effective to shield high frequency electromagnetic wave noise. In the cross-sectional views shown in FIGS. 5 to 8, illustration of the laminated structure of each shielding body is omitted.

Figure 5:
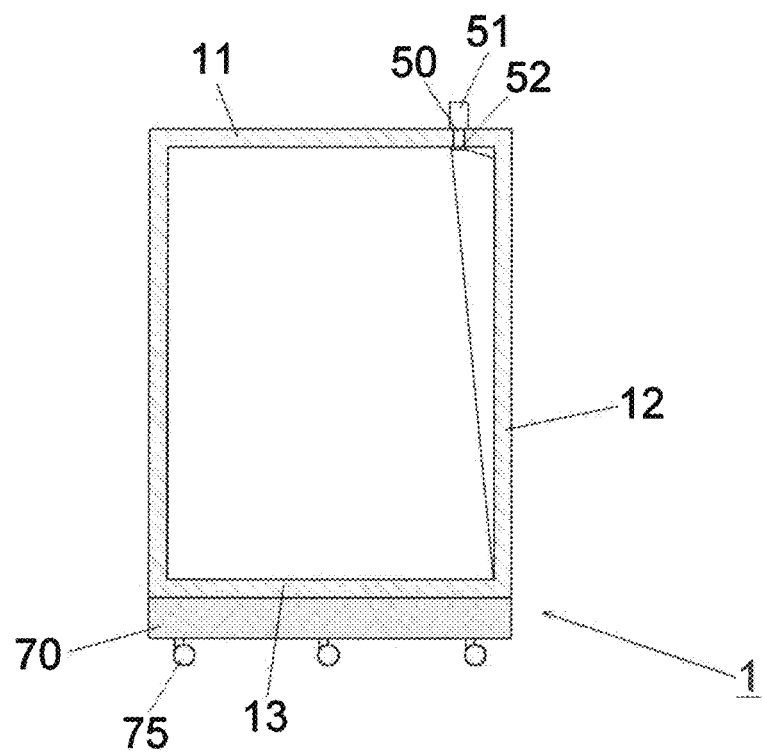
FIG. 5 is a schematic sectional view of the magnetically shielded room 1.

As shown in FIG. 5, a magnifying lens 52 is provided at an inner surface (ceiling surface of magnetically shielded room 1) of the upper shielding body 11. The magnifying lens 52 is arranged to cover a lower opening of the through hole 50. A projection device 51 is installed on an outer surface (upper surface) of the upper shielding body 11 at a position near an upper opening of the through hole 50. The magnifying lens 52 transfers an incident image from the projection device 51 through the through hole 50 to one inner side surface of the magnetically shielded room 1 (one of the inner surfaces of the side periphery shielding body 12 or an inner surface of the door 20), so that the magnifying lens 52 can magnify and project to a range that is 50% or more of the area of the one inner side surface and that includes most of the area above a line of sight of a person in the magnetically shielded room 1. The reason for this range is to allow the person inside the magnetically shielded room 1 to feel that the image is projected on most of the one inner side surface.

The magnifying lens 52 is preferably capable of projecting the image entirely on the one inner side surface. The magnifying lens 52 is not limited to a single lens, and may be a combination of a plurality of lenses.

The magnifying lens 52 is provided at a position closer to the one inner side surface as a projection target of the lens 52 than the other inner side surface as a non-projection target facing the one inner side surface as the projection target. The magnifying lens 52 is preferably provided at a position near the center in a width direction of the one inner side surface as the projection target. The image projected onto the one inner side surface by the magnifying lens 52 is preferably an image outside the magnetically shielded room 1 (an image of a landscape that was visible if there was no wall having the one inner side surface serving as the projection target).

It may be an image where the person can relax, such as a scenery. The image is preferably a moving image, but may be a still image. At least a projection range of the one inner side surface that is the projection target is preferably covered with wallpaper or material suitable for projecting the image. Covering of the projection target includes coating.

According to this embodiment of the present invention, the following effects can be obtained.

(1) Since the image from the projection device 51 is enlarged and projected by the magnifying lens 52 to the one inner side surface so that the magnifying lens 52 magnifies and projects to the range that is 50% or more of the area of the one inner side surface and that includes most of the area above a line of sight of the person in the magnetically shielded room 1, it is possible to reduce a feeling of pressure or anxiety felt by the person inside the magnetically shielded room 1.

(2) Since the magnifying lens 52 is provided at the position closer to the one inner side surface as the projection target of the lens 52 than the other inner side surface as the non-projection target facing the one inner side surface as the projection target, it can suppress that a shadow of the person inside the magnetically shielded room 1 inters into the projected image, and enables image projection to a wide range, so that it is possible to reduce effectively a feeling of pressure or anxiety felt by the person inside the magnetically shielded room 1.

(3) By making the projected image a moving image outside the magnetically shielded room 1, especially a real-time moving image, the feeling of obstruction felt by the person inside the magnetically shielded room 1 is effectively reduced, and a sense of pressure or anxiety is noticeably reduced.

(4) Since the projection device 51 is installed on the upper surface of the upper shielding body 11, a support stand that protrudes from the side periphery shielding body 12 to the side is unnecessary compared to the case where the devise 51 is installed on the side periphery shielding body 12. As a result, width and depth of magnetically shielded room 1 can be made compact.

(5) By mounting and fixing the body part of the magnetic shield room 1 including the upper shield body 11, the side periphery shield body 12 and the lower shield body 13 on the pedestal 70 having high rigidity, the weight of the bottom surface of the above body part is dispersed and stabilized, thereby making it possible to reduce the distortion of the magnetic shield room 1 at the time of moving.

(6) When the pedestal 70 is a conductor, grounding is easily made at the time of fixing the magnetic shield room 1 by electrically connecting the upper shield body 11, the side periphery shield body 12 and the lower shield body 13 (that is, the body part of the magnetic shield room 1) to the pedestal 70. That is, the pedestal 70 may be connected to an external ground connection terminal.

Second Embodiment

Figure 6:
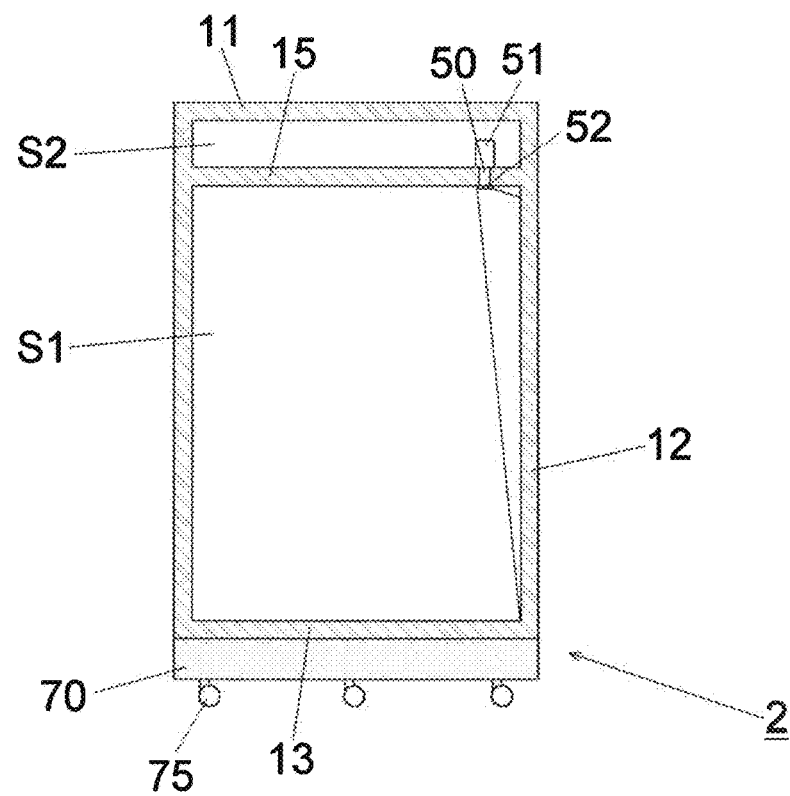
FIG. 6 is a schematic sectional view of a second embodiment of a magnetically shielded room 2 according to the present invention.

FIG. 6 is a schematic sectional view of a second embodiment of a magnetically shielded room 2 according to the present invention. The magnetically shielded room 2 has a partition member 15, and an inner space formed by an upper shield body 11, a side periphery shield body 12, a lower shield body 13, and a door 20 is divided by the partition member into first and second inner spaces S1 and S2. The partition member 15 is substantially parallel to the lower shield body 13 and divides the above inner space into upper and lower spaces. The partition member 15 is a magnetically shielding body similar with the upper shielding body 11 or the like. The lower space of the partition member 15 is the first inner space 51, and the upper space is the second inner space S2.

A projection device 51 is installed in the second inner space S2, and arranged at a position near an upper opening of the through hole 50 formed in the partition member 15. A magnifying lens 52 is arranged on an under surface of the partition member 15, and covers a lower opening of the through hole 50. The magnifying lens 52 can magnify and project to a range that is 50% or more of the area of one inner side surface of the magnetically shielded room 2 facing the first inner space S1, and that includes most of the area above a line of sight of a person in the magnetically shielded room 2. Other constitution of the second embodiment is the same as that of the first embodiment. The second embodiment also can achieve the same effect as the first embodiment. According to the second embodiment, it is convenient that the projection device 51 can be installed in the magnetic shield room 2.

Third Embodiment

Figure 7:
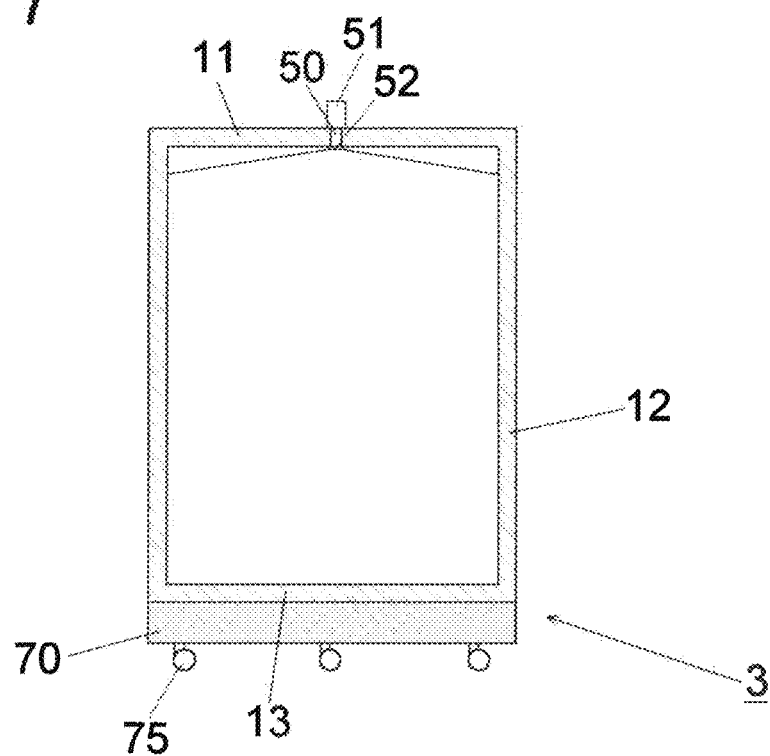
FIG. 7 is a schematic sectional view of a third embodiment of a magnetically shielded room 3 according to the present invention.

FIG. 7 is a schematic sectional view of a third embodiment of a magnetically shielded room 3 according to the present invention. In this embodiment, a magnifying lens 52 is a lens that can project in all directions (horizontal angle of view 360 degrees) and is provided near the center of a lower surface of an upper shielding body 11, so that the magnifying lens 52 can enlarge and project an image from a projection device 51 over the entire circumference (one round) of inner side surfaces of the magnetically shielded room 3. The projection range is 50% or more of the area of the entire circumference of the inner side surfaces, and includes most of the area above a line of sight of a person in the magnetically shielded room 3. Other constitution of the third embodiment is the same as that of the first embodiment. The third embodiment also can achieve the same effect as the first embodiment. According to the third embodiment, even if there is only one through hole 50 through which a projection light of the image passes, the image can be projected on the inner side surfaces of the magnetically shielded room 3 over the entire circumference, so that deterioration of magnetic shield performance can be suppressed.

Fourth Embodiment

Figure 8:
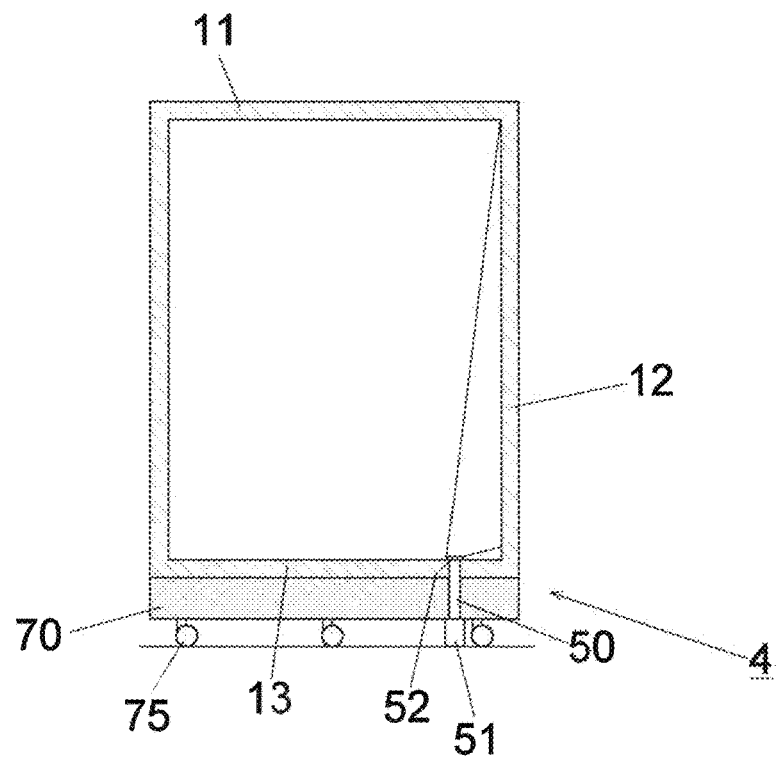
FIG. 8 is a schematic sectional view of a fourth embodiment of a magnetically shielded room 4 according to the present invention.

FIG. 8 is a schematic sectional view of a fourth embodiment of a magnetically shielded room 4 according to the present invention. In the magnetically shielded room 4, a through hole 50 penetrates a lower shielding body 13 and a pedestal 70, so that a projection light of an image incidents into the magnetically shielded room 4 through the through hole 50. A projection device 51 is installed on a floor where the magnetically shielded room 4 is placed, and the projection device 51 is positioned in a space between the pedestal 70 and the floor surface, i.e. the space created by the pedestal 70 floating against the floor surface by casters 75 (leg). The projection device 51 is provided in the vicinity of a lower opening of the through hole 50 that penetrates the lower shielding body 13 and the pedal 70. The magnifying lens 52 is provided on an upper surface of the lower shielding body 13 (an inner bottom surface of the magnetically shielded room 4) so that the lens 52 covers the upper opening of the through hole 50. Other constitution of the fourth embodiment is the same as that of the first embodiment. The fourth embodiment also can achieve the same effect as the first embodiment. According to the fourth embodiment, since the projection device 51 can be disposed on the floor surface, the projection device 51 does not protrude upward from the magnetically shielded room 4, and the magnetically shielded room 4 can be compactly installed.

Fifth Embodiment

Figure 9:
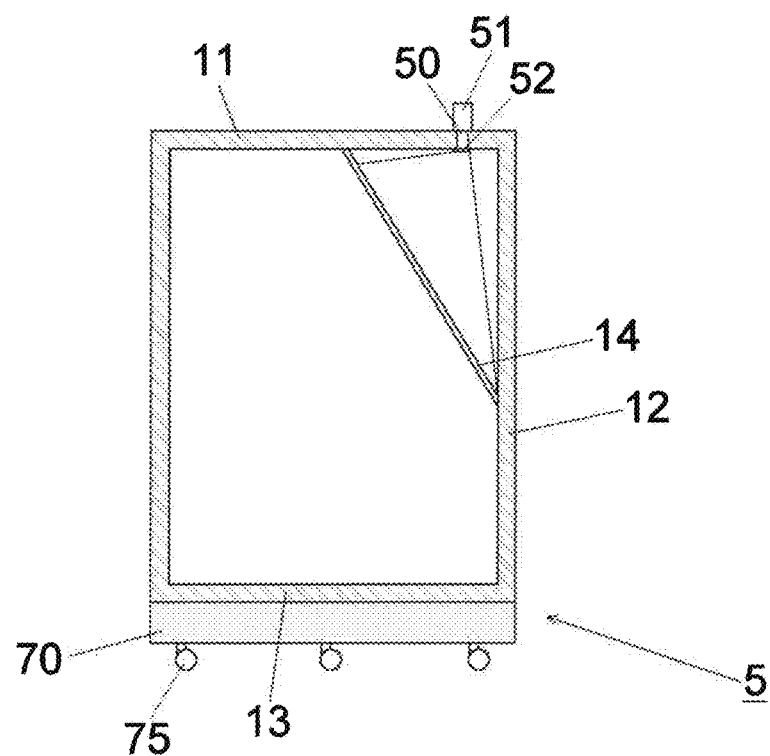
FIG. 9 is a schematic sectional view of a fifth embodiment of a magnetically shielded room 5 according to the present invention.

FIG. 9 is a schematic sectional view of a fifth embodiment of a magnetically shielded room 5 according to the present invention. The magnetically shielded room 5 includes a rear projection film 14 that is disposed to pass between one inner surface of a side periphery shielding body 12 and an inner surface of an upper shielding body 11 and extends obliquely up and down in the magnetically shielded room 5. The rear projection film 14 may be disposed to extend in the vertical direction. The rear projection film 14 is a transparent or translucent film (or sheet), and is attached to a transparent nonmagnetic plate such as an acrylic plate or a glass plate as necessary. Width of the rear projection film 14 is preferably equal to width of the one inner surface of the side periphery shielding body 12. The magnifying lens 52 is provided at a position closer to the one inner surface than the surface facing the one inner surface. The magnifying lens 52 magnifies and projects the image from the projection device 51 on the most part of the rear projection film 14 from behind the rear projection film 14 (opposite a person in the magnetically shielded room 5). Other constitution of the fifth embodiment is the same as that of the first embodiment. The fifth embodiment can also reduce the feeling of pressure or anxiety felt by the person inside the magnetically shielded room 5, like the first embodiment.

Sixth Embodiment

Figure 10:
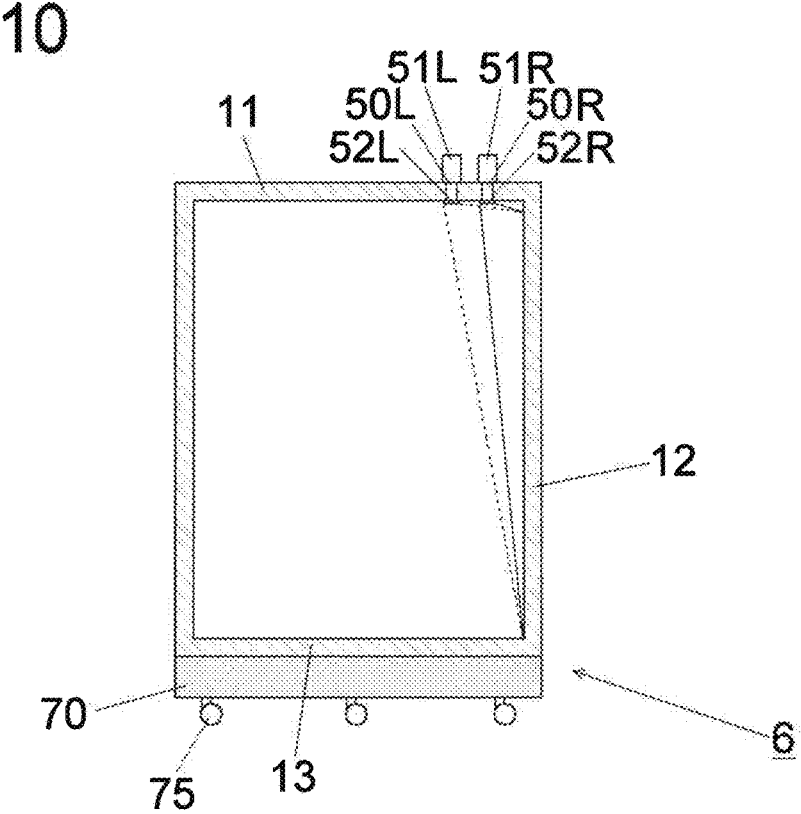
FIG. 10 is a schematic sectional view of a sixth embodiment of a magnetically shielded room 6 according to the present invention.

FIG. 10 is a schematic sectional view of a sixth embodiment of a magnetically shielded room 6 according to the present invention. Magnetically shielded room 6 is based on the configuration of the first embodiment and can project 3D picture (3D image). This will be specifically described below.

An upper shielding body 11 is provided with through holes 50R, 50L. A right-eye projection device 51R is installed at a position near an upper opening of the through hole 50R. The right-eye projection device 51R projects the image for the right eye. A right-eye magnifying lens 52R covers a lower opening of the through hole 50R, and the right-eye magnifying lens 52R magnifies and projects the incident image (image for the right eye) from the right-eye projection device 51R passing the through hole 50R to one inner side surface of the magnetically shielded room 6.

The same applies to an image for the left eye, and a left-eye projection device 51L is installed at a position near the upper opening of the through hole 50L. The left-eye projection device 51L projects the image for the left eye. A left-eye magnifying lens 52L covers a lower opening of the through hole 50L, and the left-eye magnifying lens 52L magnifies and projects the incident image (image for the left eye) from the left-eye projection device 51L passing the through hole 50L to the one inner side surface (same inner side surface as the projection destination with the right-eye magnifying lens 52R) of the magnetically shielded room 6.

The right-eye projection device 51R and the left-eye projection device 51L are installed side by side in the direction perpendicular to the inner side surface as the projection target in the illustrated example (vertical side-by-side installation), but are installed side by side in the direction parallel to the inner side surface (side-by-side installation). The right-eye magnifying lens 52R and the left-eye magnifying lens 52L polarizes the right-eye and left-eye images in different directions each other in addition to magnify, and the above-described images (right-eye image and left-eye image) polarized for the right eye and left eye respectively are projected and overlapped onto the one inner side surface.

A person inside the magnetically shielded room 6 applies so-called 3DGlasses (Glasses with different polarization directions on the left and right), so that the right eye sees the right-eye image, the left eye sees the left-eye image, and both eyes see 3D picture (3D image). The method of displaying a stereoscopic image is not limited to the polarization method (passive method). It may be a method (active shutter method (frame sequential method)) in which the right-eye image and the left-eye image are alternately projected at high speed by the right-eye projection device 51R and the left-eye projection device 51L, and on the 3DGlasses side, the left and right lenses are opened and closed at high speed in synchronization with the image to show different images to the right and left eyes. In this case, the right-eye magnifying lens 52R and the left-eye magnifying lens 52L may not polarize, and the 3DGlasses may not polarize.

Other constitution of the sixth embodiment is the same as that of the first embodiment. According to the sixth embodiment, since depth can be felt even in a narrow closed space, it is possible to further reduce the feeling of pressure or anxiety felt by a person inside the magnetically shielded room 6. Further, the modifications performed on the first embodiment in the second to fifth embodiments are applicable to the sixth embodiment.

OTHER EMBODIMENTS

In the first, second and fourth embodiments, the magnifying lens 52 may be provided corresponding to each of the two or more inner side surfaces of the magnetically shielded room. In this case, if the same number of projection devices 51 as that of the magnifying lens 52 are used, the projection range is expanded more than twice, and the effect of reducing the feeling of pressure or anxiety is enhanced. Particularly, if the magnifying lens 52 (four in total) is provided corresponding to each of the four (all) inner side surfaces of the magnetically shielded room, the image will be applied to the inner side surfaces of the magnetically shielded room over the entire circumference of four direction. Thus, a person inside can see the image from either side, and the effect of reducing the feeling of pressure or anxiety is remarkable. The same applies to the sixth embodiment.

While the invention has been described in its preferred embodiments, it is to be understood by a person having ordinary skill in the art that variations may be made on each constituent element and process of the embodiments without departing from the scope of the following claims. Variations of the invention will be described hereinafter.

The appearance of the magnetically shielded room of the present invention is not limited to a rectangular parallelepiped shape, and may be another shape such as a cylindrical shape. The door 20 is not limited to a rotary type, and may be a slide type as long as the opening of the inner space can be opened and closed.

EXPLANATIONS OF LETTERS OF NUMERALS 1-6 magnetically shielded room, 11 upper shielding body, 12 side periphery shielding body, 13 a lower shielding body, 14 rear projection film, 50, 50R, 50L through hole, 51 projection device, 51R right-eye projection device, 51L left-eye projection device,
52 magnifying lens, 52R right-eye magnifying lens,
52L left-eye magnifying lens, 70 pedestal, 75 caster (leg)

The invention claimed is:

1. A magnetically shielded room comprising:
   an upper shielding body, a side periphery shielding body, and a lower shielding body, together defining a magnetically shielded inner space; and
   a magnifying lens located in at least one of the upper shielding body and the lower shielding body, wherein the magnifying lens magnifies and transmits an image projected onto the magnifying lens from outside the magnetically shielded room to one of
   (a) at least a first inner side surface of the magnetically shielded room, and
   (b) a transparent or translucent film or sheet which extends vertically or obliquely up and down in the magnetically shielded room.

2. The magnetically shielded room according to claim 1, wherein the magnifying lens is located at a position closer to the first inner side surface, as a projection target of the lens, than a second inner side surface, which is a non-projection target facing the first inner side surface.

3. The magnetically shielded room according to claim 1, wherein a respective magnifying lens is located in a respective position corresponding to each upper side surface of a plurality of inner side surfaces of the magnetically shielded room.

4. The magnetically shielded room according to claim 1, wherein an image outside of the magnetically shielded room is projected onto and transmitted by the magnifying lens.

5. The magnetically shielded room according to claim 1, wherein the magnifying lens includes a right-eye magnifying lens that projects a right-eye image and a left-eye magnifying lens that projects a left-eye image.

6. The magnetically shielded room according to claim 1, wherein at least a projection range of the inner side surface that is a projection target of the magnifying lens is covered with a material for displaying a projected image.

7. The magnetically shielded room according to claim 1, wherein the magnetically shielded room is movable.

8. A magnetically shielded room comprising:
   an upper shielding body, a side periphery shielding body, and a lower shielding body; and
   a magnifying lens located in the upper shielding body, wherein the magnifying lens magnifies and transmits an image projected onto the magnifying lens from outside the magnetically shielded room over all of inner side surfaces of the magnetically shielded room.

9. The magnetically shielded room according to claim 8, wherein an image outside of the magnetically shielded room is projected onto and transmitted by the magnifying lens.

10. The magnetically shielded room according to claim 8, wherein the magnifying lens includes a right-eye magnifying lens that projects a right-eye image and a left-eye magnifying lens that projects a left-eye image.

11. The magnetically shielded room according to claim 8, wherein at least a projection range of the inner side surface that is a projection target of the magnifying lens is covered with a material for displaying a projected image.

12. The magnetically shielded room according to claim 8, wherein the magnetically shielded room is movable.

* * * * *